United States Patent
Shi et al.

(10) Patent No.: US 8,583,253 B1
(45) Date of Patent: Nov. 12, 2013

(54) IMPLANTABLE NEUROSTIMULATION SYSTEM AND METHOD FOR ESTIMATING ELECTRODE IMPEDANCE VALUES FOR NEUROSTIMULATION SYSTEMS

(75) Inventors: Yanwei Shi, Plano, TX (US); Robert P. Egemo, Plano, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 297 days.

(21) Appl. No.: 12/972,152

(22) Filed: Dec. 17, 2010

Related U.S. Application Data

(60) Provisional application No. 61/287,493, filed on Dec. 17, 2009.

(51) Int. Cl.
*A61N 1/36* (2006.01)

(52) U.S. Cl.
USPC ....... 607/62; 607/1; 607/2; 607/115; 607/116

(58) Field of Classification Search
USPC .................................. 607/1–2, 62, 115–116
See application file for complete search history.

(56) References Cited

U.S. PATENT DOCUMENTS

| | | | |
|---|---|---|---|
| 5,549,646 A | 8/1996 | Katz et al. | |
| 5,891,179 A | 4/1999 | Er et al. | |
| 7,047,083 B2 | 5/2006 | Gunderson et al. | |
| 7,395,119 B2 * | 7/2008 | Hagen et al. | 607/116 |
| 7,853,330 B2 | 12/2010 | Bradley et al. | |
| 2003/0176807 A1 | 9/2003 | Goetz et al. | |
| 2008/0125833 A1 * | 5/2008 | Bradley et al. | 607/60 |
| 2010/0106204 A1 | 4/2010 | Moffitt et al. | |

OTHER PUBLICATIONS

Medtronic, "Medtronic Pain Therapy, Using neurostimulation for chronic pain," Information for prescribers, Sep. 2007, 1-25.

* cited by examiner

*Primary Examiner* — Deborah Malamud

(57) ABSTRACT

In one embodiment, a method, for estimating electrode resistance values, comprises: calculating an aggregate resistance value for each electrode in a group of electrodes of an implantable stimulation lead of the electrical stimulation system, wherein the calculating, for each electrode, comprises: (i) setting a respective electrode in the group of electrodes as an anode; (ii) setting electrodes in the group of electrodes other than the respective electrodes as cathodes; (iii) applying a predetermined electrical signal through the group of the electrodes using a pulse generator of the electrical stimulation system; (iv) measuring current flow or voltage resulting from application of the predetermined electrical signal through the group of the electrodes; (v) calculating the aggregate resistance value for the respective electrode in response to the measuring; calculating an individual resistance value for each electrode of the group of electrodes using the set of aggregate resistance values for the group of electrodes.

9 Claims, 3 Drawing Sheets

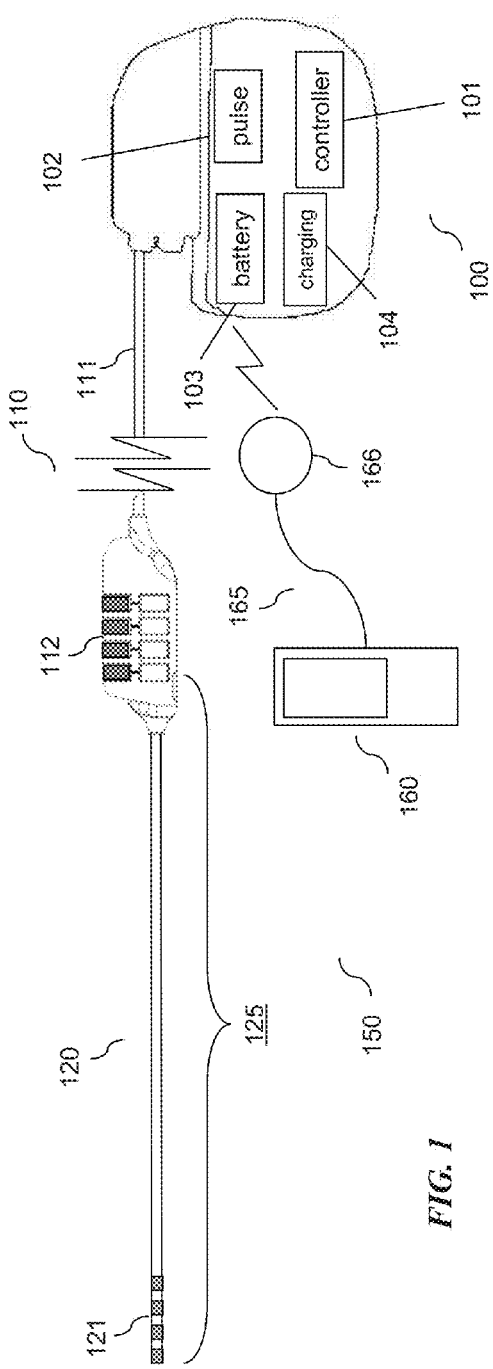
FIG. 1
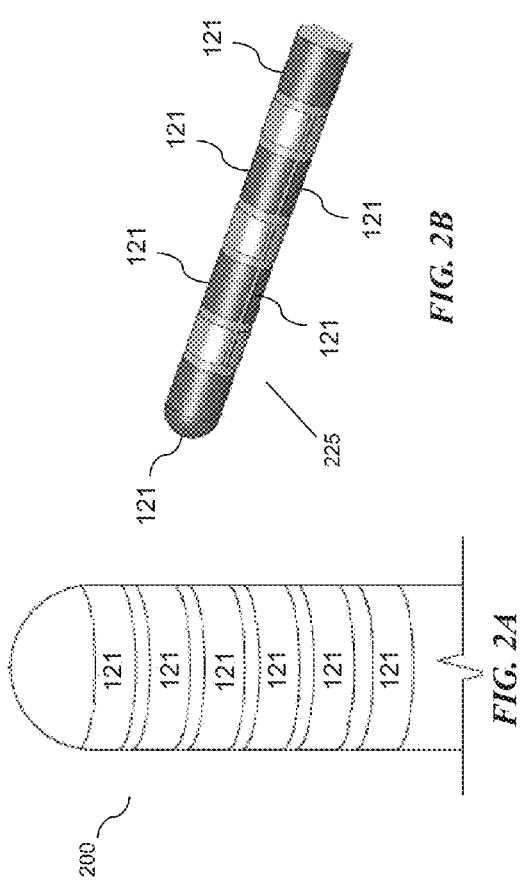
FIG. 2A
FIG. 2B
FIG. 2C

IMPLANTABLE NEUROSTIMULATION SYSTEM AND METHOD FOR ESTIMATING ELECTRODE IMPEDANCE VALUES FOR NEUROSTIMULATION SYSTEMS

CROSS-REFERENCE TO RELATED APPLICATIONS

This application claims the benefit of U.S. Provisional Application No. 61/287,493, filed Dec. 17, 2009, which is incorporated herein by reference.

TECHNICAL FIELD

This application is generally related to implantable neurostimulation systems and methods of estimating electrode impedance values for neurostimulation systems.

BACKGROUND

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

The stimulation therapy provided by implantable neurostimulation systems may be affected by electrode impedance. Known neurostimulation systems include functionality to test the impedance of the various electrodes of the stimulation lead(s). The testing may identify short circuits and open circuits. Also, the impedance testing may be utilized for other purposes. For example, the amplitude of applied pulses may be adjusted in response to the impedance testing. Since the accuracy of the impedance testing may vary depending upon the details of the testing methodology, the effectiveness of adjustments in stimulation therapy may also vary depending upon the impedance testing methodology.

SUMMARY

In one embodiment, a method, for estimating electrode resistance values, comprises: calculating an aggregate resistance value for each electrode in a group of electrodes of an implantable stimulation lead of the electrical stimulation system, wherein the calculating, for each electrode, comprises: (i) setting a respective electrode in the group of electrodes as an anode; (ii) setting electrodes in the group of electrodes other than the respective electrodes as cathodes; (iii) applying a predetermined electrical signal through the group of the electrodes using a pulse generator of the electrical stimulation system; (iv) measuring current flow or voltage resulting from application of the predetermined electrical signal through the group of the electrodes; (v) calculating the aggregate resistance value for the respective electrode in response to the measuring; calculating an individual resistance value for each electrode of the group of electrodes using the set of aggregate resistance values for the group of electrodes.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 1 depicts a stimulation system according to one representative embodiment.

FIGS. 2A-2C depict respective stimulation leads that may be used in the system of FIG. 1 according to one representative embodiment.

DETAILED DESCRIPTION

Figure 3:
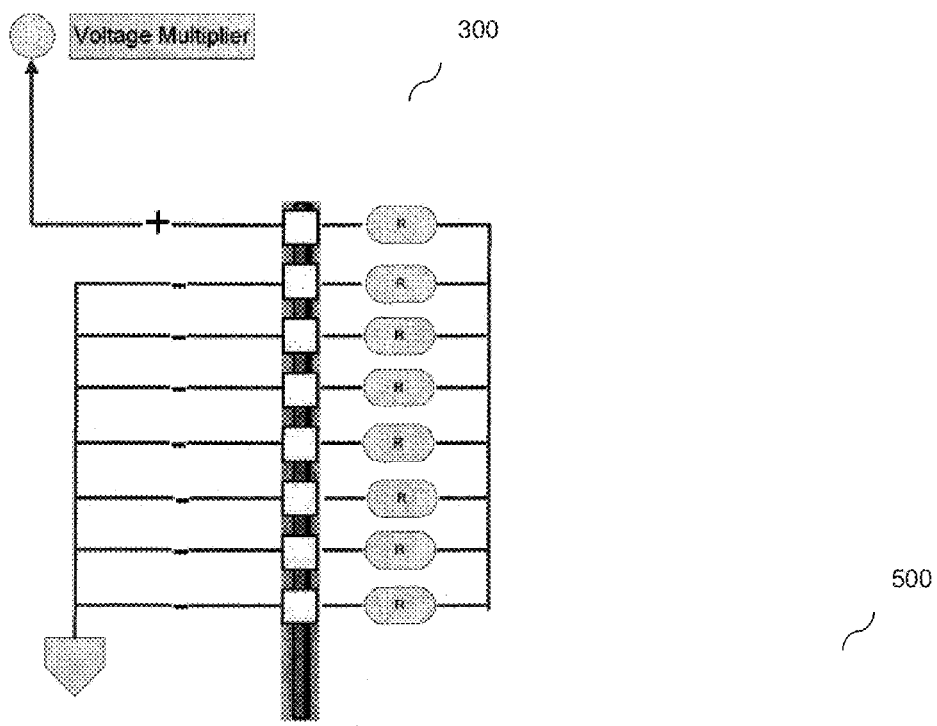
FIG. 3 depicts a circuit model for estimating electrode resistance values according to one representative embodiment.

FIG. 1 depicts stimulation system 150 that generates electrical pulses for application to tissue of a patient according to one embodiment. In one embodiment, system 150 is adapted to generate electrical pulses and deliver the pulses to tissue of the patient. For example, system 150 may be adapted to stimulation spinal cord tissue, peripheral nerve tissue, deep brain tissue, cortical tissue, cardiac tissue, digestive tissue, pelvic floor tissue, or any other suitable tissue within a patient's body.

System 150 includes implantable pulse generator 100 that is adapted to generate electrical pulses for application to tissue of a patient. Implantable pulse generator 100 typically comprises a metallic housing that encloses pulse generating circuitry 102, controller 101, charging coil (not shown), battery 103, far-field and/or near field communication circuitry (not shown), battery charging circuitry 104, etc. of the device. Although an implantable pulse generator is shown for the embodiment of FIG. 1, an external pulse generator (e.g., a "trial" stimulator) may alternatively be employed. The controller 101 typically includes a microcontroller or other suitable processor for controlling the various other components of the device. Software code is typically stored in memory of the pulse generator 100 for execution by the microcontroller or processor to control the various components of the device.

A processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 100. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation system 150 further comprises one or more stimulation leads 120. Stimulation lead 120 comprises a lead body of insulative material about a plurality of conductors that extend from a proximal end of lead 120 to its distal end. The conductors electrically couple a plurality of electrodes 121 to a plurality of terminals (not shown) of lead 120. The terminals are adapted to receive electrical pulses and the electrodes 121 are adapted to apply stimulation pulses to tissue of the patient. Also, sensing of physiological signals may occur through electrodes 121, the conductors, and the terminals. Additionally or alternatively, various sensors (not shown) may be located near the distal end of stimulation lead 120 and electrically coupled to terminals through conductors within the lead body 111.

FIGS. 2A-2C respectively depict stimulation portions 200, 225, and 250 for inclusion at the distal end of lead 120. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Provisional Patent Application Ser. No. 61/247,360, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Stimulation system 150 optionally comprises extension lead 110. Extension lead 110 is adapted to connect between pulse generator 100 and stimulation lead 120. That is, electrical pulses are generated by pulse generator 100 and provided to extension lead 110 via a plurality of terminals (not shown) on the proximal end of extension lead 110. The electrical pulses are conducted through conductors within lead body 111 to housing 112. Housing 112 includes a plurality of electrical connectors (e.g., "Bal-Seal" connectors) that are adapted to connect to the terminals of lead 120. Thereby, the pulses originating from pulse generator 100 and conducted through the conductors of lead body 111 are provided to stimulation lead 120. The pulses are then conducted through the conductors of lead 120 and applied to tissue of a patient via electrodes 121.

In practice, stimulation lead 120 is implanted within a suitable location within a patient adjacent to tissue of a patient to treat the patient's particular disorder(s). The lead body extends away from the implant site and is, eventually, tunneled underneath the skin to a secondary location. Housing 112 of extension lead 110 is coupled to the terminals of lead 120 at the secondary location and is implanted at that secondary location. Lead body 111 of extension lead 110 is tunneled to a third location for connection with pulse generator 100 (which is implanted at the third location).

Controller device 160 may be implemented to recharge battery 103 of pulse generator 100 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery 103 by charging circuitry 104. Charging circuitry 104 may also communicate status messages to controller 160 during charging operations using pulse-loading or any other suitable technique. For example, controller 160 may communicate the coupling status, charging status, charge completion status, etc.

External controller device 160 is also a device that permits the operations of pulse generator 100 to be controlled by user after pulse generator 100 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 100.

Controller device 160 preferably provides one or more user interfaces to allow the user to operate pulse generator 100 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 100 modifies its internal parameters in response to the control signals from controller device 160 to vary the stimulation characteristics of stimulation pulses transmitted through stimulation lead 120 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

It is known to provide low levels of currents through various electrodes during conventional testing procedures. Such testing procedures assist in identifying short circuits, open circuits, and certain other electrode conditions. Also, the testing procedure provides an estimate of effective electrode resistance. However, known testing procedures involve some degree of inaccuracy. Some representative embodiments provide a process for estimating electrode resistance in a manner that is believed to be more accurate. Also, some representative embodiments adapt stimulation system 150 to automatically perform the electrode resistance estimation.

FIG. 3 depicts circuit model 300 that is used to approximate or model the circuit/electrode configuration for estimation of electrode resistance according to some representative embodiments. In some embodiments, one electrode of a group of electrodes to be tested is set to function as an anode. All other electrodes of the group are set to function as cathodes. The circuit model assumes that the cathodes are connected in parallel to a return current path through tissue of the patient. A voltage is applied and current flows through tissue of the patient between the anode and cathodes. The magnitude of the current flow is measured and an effective aggregate resistance for the circuit is calculated from the applied voltage and the current flow. This process is repeated for each electrode such that each electrode is set to function as an anode with all other electrodes set as cathodes and a respective aggregate resistance value is calculated. From these sets of calculated aggregate resistance values, an individual resistance value for each electrode is calculated as will be discussed below.

Figure 4:
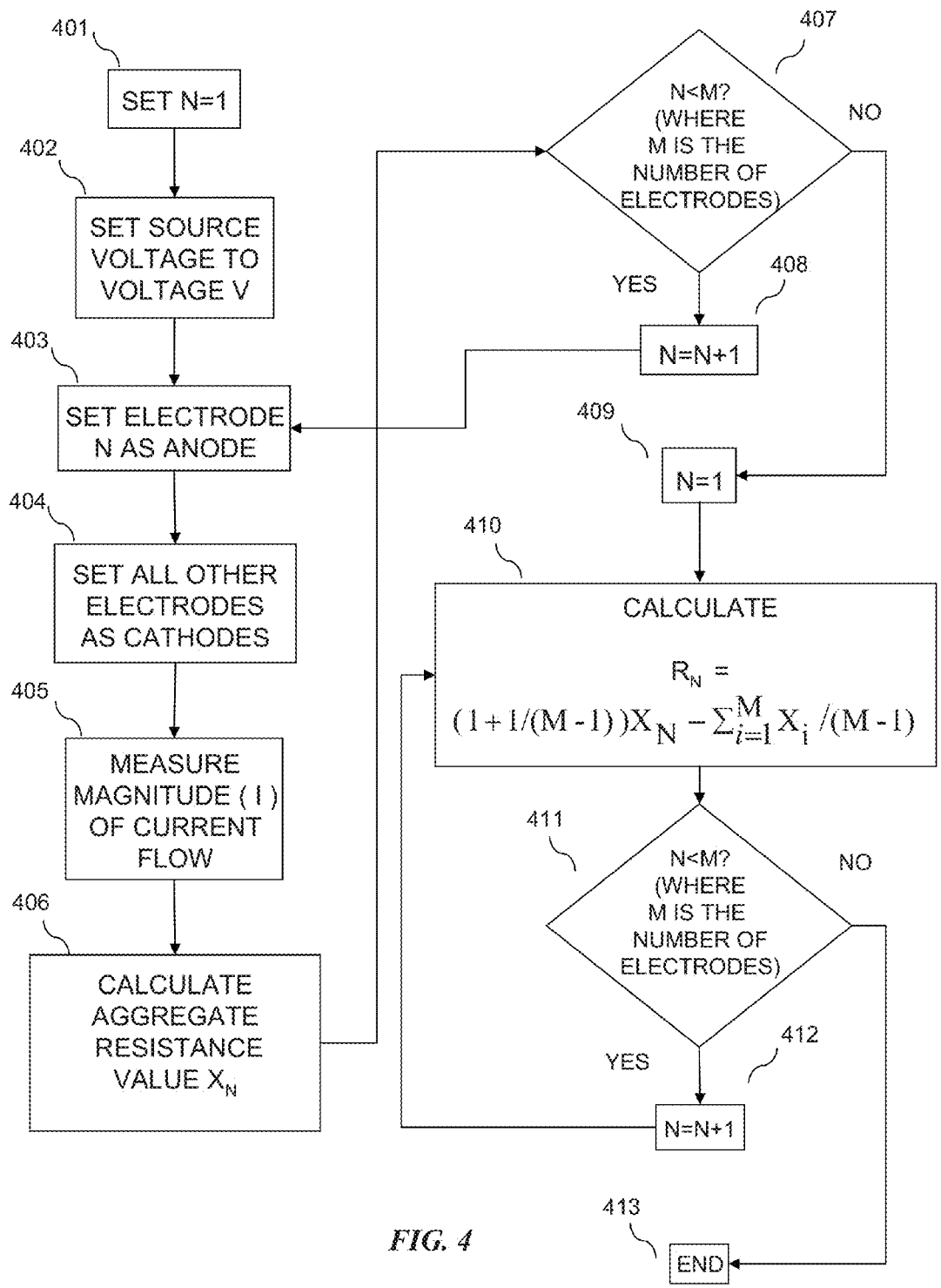
FIG. 4 depicts a flowchart for calculating electrode resistance values according to one representative embodiment.

FIG. 4 depicts a flowchart of a process for calculating a respective individual resistance value for each electrode of a group of electrodes according to one representative embodiment. In some embodiments, the process of FIG. 4 is implemented by utilizing, in part, suitable software in external controller device 160. The software may utilize a suitable control loop to perform the various tasks for each electrode and then calculate the desired individual resistance values.

Also, the software may utilize the wireless communication or telemetry functionality of device 160 to communicate appropriate commands to IPG 100. The commands cause IPG 100 to apply stimulation through selected electrode combinations. Also, device 160 may cause IPG 100 to communicate respective measurements (current measurements) back to device 160 via the wireless functionality of the devices. The software of device 160 may utilize the communicated data to calculate the individual resistance values for each electrode of the group of electrodes. In some embodiments, the group of electrodes is the total set of electrodes for a given stimulation lead. In an alternative embodiment, the group of electrodes is a lesser subset of the total set of electrodes of the stimulation lead. The electrodes selected for the resistance calculation may be selected by the user through a suitable interface screen of device 160 (e.g., "check-boxes" 501 in screen 500 in FIG. 5 may be presented to the user for selection of the electrodes for testing).

In 401, the variable "N" is set to equal one.

In 402, the source voltage of the IPG is set to equal the value V. In one embodiment, the value is set to equal an amount that is sub-threshold (i.e., will not have a perceptible effect on the patient), although supra-threshold levels could be alternatively be applied.

In 403, electrode number N is set to function as an anode.

In 404, all other electrodes of the group of electrodes are set to function as cathodes.

In 405, the magnitude of the current flow between the electrodes is measured. In another embodiment, a constant current may be applied and the resulting voltage measured.

In 406, the aggregate resistance ($X_N$) is calculated for the respective electrode combination where the Nth electrode is a cathode and all other electrodes are anodes using the voltage and/or current values. Any suitable circuit model and/or formula for modeling the flow of current through the electrodes and the tissue of the patient may be employed to calculate or estimate the electrode resistance.

In 407, a logical comparison is made to determine whether N<M, where M is the total number of electrodes in the group of electrodes to be tested.

If so, the process flow proceeds to 408, where the value of N is incremented (N=N+1). From 408, the process flow returns to 403. If N is equal to M, the process flow proceeds to 409.

In 409, the value of the variable N is set to equal 1.

In 410, the individual resistance value ($R_N$) for electrode N is calculated according to the following formula:

$$(1+1/(M-1))X_N - \Sigma_{i=1}^{M} X_i/(M-1)$$

In 411, a logical comparison is made to determine whether N<M. If so, the process flow proceeds to 412. In 412, the value of N is incremented (N=N+1). From 412, the process flow returns to 410. If N=M, the process flow proceeds to 413 to end.

Figure 5:
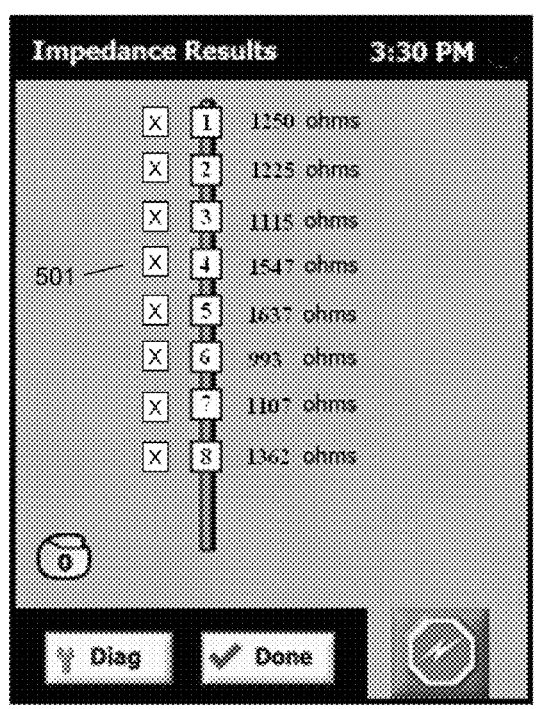
FIG. 5 depicts an example screen for displaying electrode resistance values.

The calculated resistance values may be stored and/or displayed in a suitable screen on device 160 for review by a clinician or other user. FIG. 5 depicts example screen 500 displaying resistance values according to one representative embodiment.

In another embodiment, the calculation of the resistance values for the electrodes may be performed entirely within implantable pulse generator 100. In such an embodiment, implantable pulse generator 100 may employ the calculated resistance values in a feedback loop to control stimulation applied to the patient. A change in resistance values may occur over a longer period of time and may be related to changes in tissue surrounding the electrodes (e.g., fibrosis or scarring). In a feedback loop for this type of stimulation, the amplitude of pulses may be increased due to detected changes in resistance values over time. Alternatively, the resistance values for electrodes of a spinal cord stimulation (SCS) lead may change in response to a change in posture by the patient. Different electrode combinations and different pulse amplitudes (different stimulation "programs") may be defined for different postures of the patient (from standing to sitting or reclining, etc.). Thereby a feedback loop may be implemented whereby when a suitable change in resistance is detected, the change in posture is detected and a suitable change in the stimulation program is made. The resistance calculation functionality and/or the feedback loop may be implemented by storing suitable software code in controller 101 or in other memory of implantable pulse generator 100 according to some embodiments.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method for estimating electrode resistance values for electrodes of an electrical stimulation system for stimulation of tissue of a patient, the method comprising:
    calculating an aggregate resistance value for each electrode in a group of electrodes of an implantable stimulation lead of the electrical stimulation system, wherein the calculating, for each electrode, comprises:
        (i) setting a respective electrode in the group of electrodes as an anode;
        (ii) setting electrodes in the group of electrodes other than the respective electrodes as cathodes;
        (iii) applying a predetermined electrical signal through the group of electrodes using a pulse generator of the electrical stimulation system;
        (iv) measuring current flow or voltage resulting from application of the predetermined electrical signal through the group of the electrodes;
        (v) calculating the aggregate resistance value for the respective electrode in response to the measuring;
    calculating an individual resistance value for each electrode of the group of electrodes using the set of aggregate resistance values for the group of electrodes, wherein the calculating calculates the individual resistance value for each electrode using the following formula:

$$(1+1/(M-1))X_N - \Sigma_{i=1}^{M} X_i/(M-1)$$

where $X_i$ is the aggregate resistance value for the $i^{th}$ electrode and M is the number of electrodes in the group of electrodes.

2. The method of claim 1 wherein the group of electrodes are ring electrodes of a percutaneous lead.

3. The method of claim 1 wherein the applying comprises applying a current signal and measuring a resulting voltage.

4. The method of claim 1 wherein the applying comprises applying a voltage signal and measuring a resulting current.

5. The method of claim 1 wherein the predetermined signal is sub-threshold.

6. The method of claim 1 wherein the predetermined signal is supra-threshold.

7. The method of claim 1 further comprising:
    displaying a screen that provides information indicative of a resistance of each electrode of the group of electrodes on an external controller of the electrical stimulation system.

8. The method of claim 1 further comprising:
    automatically altering a current stimulation therapy applied to the patient by the pulse generator in response to the calculating.

9. The method of claim 8 wherein the automatically altering comprises:
    changing from a first stimulation program to a second stimulation program.

* * * * *